United States Patent [19]

Baker

[11] Patent Number: 4,816,468

[45] Date of Patent: * Mar. 28, 1989

[54] 5-CYANOPYRIDINE-2-DIAZOHYDROXIDE, BASIC SALTS AND USE

[75] Inventor: David C. Baker, Tuscaloosa, Ala.

[73] Assignee: The University of Alabama, Tuscaloosa, Ala.

[*] Notice: The portion of the term of this patent subsequent to Jan. 13, 2004 has been disclaimed.

[21] Appl. No.: 872,892

[22] Filed: Jun. 11, 1986

Related U.S. Application Data

[62] Division of Ser. No. 670,203, Nov. 13, 1984, Pat. No. 4,636,564.

[51] Int. Cl.$^4$ ............................................. A61K 31/44
[52] U.S. Cl. ..................................... 514/344; 546/289
[58] Field of Search ................. 514/344; 546/289, 312

[56] References Cited

U.S. PATENT DOCUMENTS 4,636,564 1/1987 Baker et al. .................. 546/289

OTHER PUBLICATIONS

Goldin, A. et al., "Progress Report on Screening Program", Cancer Treatment Reviews (1980) pp. 167–176.
Bunton, C. A. et al, "Decomposition of Pyridine-2- and -4-diazotates", J.A.C.S., 1974, 96, pp. 3267–3275.

Primary Examiner—Jane T. Fan
Attorney, Agent, or Firm—Krass & Young

[57] ABSTRACT

The title compounds are provided as well as a method for their production, pharmaceutical compositions comprising the compounds, and methods of treatment using the compounds in dosage form. The compounds of the invention have pharmacological properties and are useful cytostatic agents and cell growth inhibiting agents.

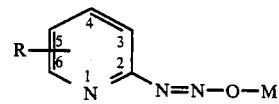

10 Claims, No Drawings

5-CYANOPYRIDINE-2-DIAZOHYDROXIDE, BASIC SALTS AND USE

This invention was made with Government support under NCI Contract No. NO1-CM-27571 awarded by the Department of Health and Human Services. The Government has certain rights in this invention.

REFERENCE TO RELATED PATENT

This application is a division of Ser. No. 670,203 filed Nov. 13, 1984, now U.S. Pat. No. 4,636,564 dated Jan. 13, 1987.

TECHNICAL FIELD

The invention relates to novel chemical compounds, that are cyanopyridine-2-diazohydroxide, basic salt compounds, to a method for their production, to pharmaceutical compositions comprising the compounds, and to methods of treatment using the compounds in dosage form. The novel compounds of the invention have pharmacological properties and are useful pharmacological agents, particularly cytostatic agents and cell growth inhibiting agents.

BACKGROUND OF THE INVENTION

Pyridine-2-diazohydroxide salt compounds (pyridine-2-diazotate compounds) are known in the literature, for example, as described by Bunton, Minch and Wolfe, *J. Am. Chem. Soc.*, 1974, 96, 3267-3275.

SUMMARY OF THE INVENTION

The invention in one aspect relates to novel cyanopyridine-2-diazohydroxide compounds having in salt form the structural formula:

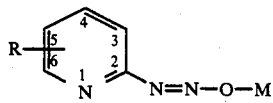

where R is a 5-CN group and M is a molar equivalent of an alkali metal (Group 1a metal), preferably sodium or potassium, or a half-equivalent of an alkaline earth metal (Group 2a metal), preferable calcium or magnesium. The compounds in pure form are solids that typically are stable to storage. By way of illustration in this regard concerning the preferred sodium salt compound, when formulated in aqueous solution at pH 7.4, the compound is stable with a half-life of about three hours, whereas the corresponding unsubstituted pyridine-2-diazotate sodium salt in aqueous solution at pH 7.4 has a half-life of only about two minutes. The compounds can exist in the syn and anti forms, and the invention contemplates both of these forms and mixtures thereof.

Process for Preparing a Basic Salt of 5-Cyanopyridine-2-diazohydroxide

The invention in one method aspect includes a process for preparing a 5-cyanopyridine-2-diazohydroxide, alkali metal or alkaline earth metal salt comprising reacting 2-amino-5-cyanopyridine and a base contained in an inert solvent, treating the reaction mixture with alkyl nitrite until diazotiztion is complete, and isolating the product from the reaction mixture in salt form.

The method is subject to considerable variation both in reactants and reaction conditions, preferably using substantially equimolar amounts of the reactants. Any of various bases can be used including alkali metal alkoxides, amides and organometallic compounds. Sodium amide is a preferred base and potassium amide can also be used. Lower ($C_1$ to $C_4$) alkyl lithium or sodium compounds are preferred organometallic bases. To convert the metal ion to a different metal ion for purposes of isolating the thus converted metal salt product, ion exchange chromatography is suitably employed preferably using the appropriate metal salt column of, for example, a sulfonic acid cation-exchanged resin. The alkyl nitrite reagent suitably is selected from lower alkyl ($C_1$ to $C_6$) nitrites which include, for example, methyl, ethyl, propyl, n-butyl, and n-pentyl nitrites. Isoamyl nitrite is a preferred nitrite. The solvent suitably comprises tetrahydrofuran (THF), ethyl ether, dioxane, dimethoxyethane or other alkyl mono-, di- or polyether solvent, THF being a preferred solvent. The reaction temperature is not critical. Temperatures in the range from 10 to 100 degrees C. can suitably be used, temperatures in the range of about 18 to about 28 degrees C. being preferred. Reaction times of from about 15 to 20 hours are generally required.

The invention in another composition aspect relates to a pharmaceutical composition for inhibiting the growth of cells comprising a cell growth inhibiting amount of 5-cyanopyridine-2-diazohydroxide, alkali metal or alkaline earth metal salt, preferably the sodium salt, potassium salt, calcium salt, or magnesium salt, and a pharmaceutically acceptable carrier.

The invention in its method aspect relates to a method for inhibiting the growth of cells in a mammal which comprises administering a cell growth inhibiting amount of 5-cyanopyridine-2-diazohydroxide, alkali metal or alkaline earth metal salt, preferably the sodium salt, potassium salt, calcium salt, or magnesium salt, in dosage form to an animal in need thereof.

PHYSICAL AND PHARMACOLOGICAL PROPERTIES OF THE COMPOUNDS

The compounds of the invention are stable solids, as indicated, and form relatively stable solutions at alkaline pH such as pH 7.4 and higher. The compounds have cytostatic and cytotoxic properties (i.e., cell growth inhibiting properties) and are useful as pharmacological agents in dosage form for animals as exemplified by rodents.

The activity of the compounds of the invention and their use are established by art-recognized protocols that are conventional per se. One such test protocol is the in vivo lymphocytic (leukemia P388) test. The animals used are either male or female $CD_2F_1$ mice, six or seven animals per test group. The cell transplant is by intraperitoneal injection of dilute ascitic fluid containing cells of lymphocytic leukemia P388. The test compound is administered intraperitoneally once daily for five consecutive days at various doses following cell innoculation. The animals are weighed and survivors are recorded on a regular basis for 30 days. A ratio of survival time for treated (T)/control (C) animals is calculated. A criterion for efficacy is a ratio T/C times 100 greater than or equal to 125. In this test, 5-cyanopyridine-2-diazohydroxide, sodium salt (which is typical in this respect of the salt compounds of the invention) was effective, at a dosage of 25 mg/kg of body weight, in providing a T/C value greatly in excess of the minimum criterion, namely a T/C value of 268.

PREPARATION OF PHARMACEUTICAL COMPOSITIONS

When used as pharmacological agents or pharmaceutical compositions, the compounds of the invention can be prepared and administered in any of a wide variety of topical, oral, and parenteral dosage forms.

For preparing pharmaceutical compositions, one uses an inert, pharmaceutically acceptable carrier which carrier can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the compound is mixed with carrier having the necessary binding properties in suitable proportion and compacted in the shape and size desired. The powders and tablets preferably contain from 5 or 20 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, e.g. natural or synthetic gums, resins, methyl cellulose, sodium carboxymethyl cellulose, and other suspending agents.

Topical preparations include dusting powders, creams, lotions, gels, and sprays. These various topical prepartions may be formulated by well-known procedures. See for example Remington's Pharmaceutical Sciences, Chapter 43, 14th Ed., Mack Publishing Co., Easton, Pa. 18042, USA.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself ot it can be the appropriate number of any of these packaged forms.

The quantity of active compound in a unit dose of preparation may be varied or adjusted from 50 mg to 500 mg according to the particular application and the potency of the active ingredient.

In therapeutic use as pharmacological agents the compound utilized in the pharmaceutical method of this invention is administered at the initial dosage of about 0.1 mg to about 50 mg per kilogram. A dose range of about 0.5 mg to about 10 mg per kilogram is preferred. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compound may also be administered parenterally or intraperitoneally. Solutions of the compound can be prepared in water mixed if desired with a surfactant such as hydroxypropylcellulose. Dispersions can also be prepared in glycerol, liquid polyethylene glycols, and mixtures thereof and in oils. Under ordinary conditions of storage and use, these preparations contain preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), N,N-dimethylacetamide, suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by sterilization accomplished by filtering. Generally, dispersions are prepared by incorporating the various sterilized active ingredient into a sterile vehicle which contains the basic dispersion medium and the required other ingredients from those enumerated above. In the case of the sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the active ingredient, its use in the therapeutic compositions is contemplated. Supplementary active ingredients can also be incorporated into the compositions.

The principal active ingredient is compounded for convenient and effective administration in effective amounts with a suitable pharmaceutically acceptable carrier in unit dosage form as hereinbefore disclosed. A unit dosage form can, for example, contain the principal active compound in amounts ranging from about 0.1 to about 500 mg, with from about 0.5 to about 250 mg being preferred. Expressed in proportions, the compound is generally present in from about 0.1 to about 500 mg/mL of carrier. In the case of compositions containing supplementary active ingredients, the dosages are determined by reference to the usual dose and the manner of administration of the said ingredients. The daily parenteral doses ranges from 0.1 mg/kg to 10 mg/kg. The preferred daily dose range is 0.3 mg/kg to 10 mg/kg.

The invention and the best mode of practicing the same are illustrated by the following examples.

EXAMPLE 1

5-Cyanopyridine-2-diazohydroxide, sodium salt 1.6 Grams (0.0134 mol) of 5-cyano-2-aminopyridine (prepared according to the procedure of P. Z. Gregory, S. J. Holt and R. Slack, *J. Chem. Soc.* 1947, 87) is added to a suspension of 0.52 g (0.0134 mol) of sodium amide in 50 mL of dry tetrahydrofuran (THF) and stirred vigorously for 30 min under dry nitrogen to give a light yellow-colored mixture. To this suspension is added 1.79 mL (0.0134 mol) of isoamyl nitrite in 5 mL of THF, and the resulting yellow mixture is stirred at ca. 23° C. for 12 h, filtered, and the title product which is a yellow solid is collected and recrystallized from methanol/ether. Yield: 1.60 g (61.4%).

$^1$H NMR (DMSOd$_6$): $\delta$7.54 (d, 1H, H-3, J=8.8 Hz), 7.86 (m, 1H, H-4), 8.63 (d, 1H, H-6, J=2.0 Hz).

By addition of a drop of trifluoroacetic acid (TFA): $\delta$6.43 (d, 1H, H-3, J=9.6 Hz), 7.70 (m, 1H, H-4), 8.20 (d, 1H, H-6, J=2.4 Hz).

IR (KBr): 3400 cm$^{-1}$, 2230 cm$^{-1}$ (C≡N) Strong peaks at 1595, 1470, 1340, 1240 cm$^{-1}$. Calcd: Na 13.51% Found: 14.92%.

EXAMPLE 2

5-Cyanopyridine-2-diazohydroxide, sodium salt 3.57 Grams (0.03 mol) of 5-cyano-2-aminopyridine is added to a suspension of 1.07 g (0.03 mol) of sodium amide in 60 mL of dry THF under dry nitrogen. The resulting white mixture is stirred at room temperature for an additional 30 min, followed by dropwise addition of 4.02 mL (0.03 mol) of isoamyl nitrite. The mixture turns gradually to bright yellow and stirring is continued for another 15 h. The resulting title product, which is a yellow solid, is collected after filtration, washed with THF (2×20 mL) and dry ether (2×30 mL) and purified first by recrystallization from methanol/ether and then by passing through an ion-exchange column containing resin Amberlite IR-120 (sodium salt of sulphonic acid); Yield 2.5 g (49%).

$^1$H NMR (DMSOd$_6$): $\delta$7.59 (d, 1H, H-3, J=8.7 Hz), 7.86 (dd, 1H, H-4, J=8.7, 2.1 Hz), 8.62 (d, 1H, H-6, J=2.1 Hz) IR (KBr): 3400 cm$^{-1}$, 2230 cm$^{-1}$ (C≡N) Peaks at 1595, 1260 cm$^{-1}$

EXAMPLE 2a

5-Cyanopyridine-2-diazohydroxide, Potassium Salt

The title product is produced by the same salt forming procedure of Example 2 except that the ion exchange is carried out using resin which is in the potassium salt form.

EXAMPLE 2b

5-Cyanopyridine-2-diazohydroxide, Calcium Salt

The title product is produced by the same salt forming procedure of Example 2 except that the ion exchange is carried out using resin which is in the calcium salt form.

EXAMPLE 2c

5-Cyanopyridine-2-diazohydroxide, Magnesium Salt

The title product is produced by the same salt forming procedure of Example 2 except that the ion exchange is carried out using resin which is in the magnesium salt form.

PHARMACEUTICAL COMPOSITIONS

The following representative Examples 3 through 7, are given as illustrative pharmaceutical compositions utilizing different carriers. In these examples, Example 3 illustrates the use of the compounds of the invention in injectables suitable for intravenous injection. Example 4 describes an oral syrup preparation, Example 5 an oral capsule preparation and Example 6, oral tablets. Example 7 is directed to use of the compounds of the invention in suitable suppositories. For Examples 3 through 7, the ingredients are listed followed by the methods of preparing the compositions.

EXAMPLE 3

INJECTABLES 5-cyanopyridine-2-diazohydroxide, sodium salt 125 mg-500 mg

Water for Injection USP q.s.

The salt compound is dissolved in the water and passed through a 0.22 micron filter. The filtered solution is added to ampoules or vials, sealed and sterilized.

EXAMPLE 4

Syrup 250 mg Active ingredient/5 ml syrup 5-cyanopyridine-2-diazohydroxide, potassium salt: 25 g Purified Water USP: 200 ml Cherry Syrup q.s. or: 1000 ml The salt compound is dissolved in the water and to this solution the syrup is added with mild stirring.

EXAMPLE 5

CAPSULES 50 mg, 125 mg or 500 mg 5-cyanopyridine-2-diazohydroxide, calcium salt: 500 g Lactose USP. Anhydrous q.s. or: 200 g Sterotex Powder HM: 5 g Combine the salt and the lactose in a twinshell blender equipped with an intensifier bar. Tumble blend for two minutes, blend for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg, 352.5 mg or 705 mg of the blend, respectively, for the 50 mg., 125 mg and 500 mg containing capsules.

EXAMPLE 6

TABLETS 50 mg, 100 mg or 250 mg 5-cyanopyridine-2-diazohydroxide, magnesium salt: 250 g
Corn Starch NF: 200.0 g
Cellulose, Microcrystalline: 46.0 g
Sterotex Powder HM: 4.0 g
Purified Water q.s. or: 300.0 ml Combine the corn starch, the cellulose and the salt compound together in a planetary mixer and mix for two minutes. Add the water to this combination and mix for one minute. The resulting mix is spread on trays and dried until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tablets of the total mix are formed with appropriate sized punches for the 50 mg, 125 mg or 250 mg containing tablets.

EXAMPLE 7

SUPPOSITORIES 125 mg, 250 mg or 500 mg per 3 g 5-cyanopyridine-2-diazohydroxide, sodium salt: 125 mg 250 mg 500 mg
1540 Polyethylene Glycol: 1925 mg 1750 mg 1400 mg
8000 Polyethylene Glycol: 825 mg 750 mg 600 mg Melt the Polyethylene Glycol 1540 and the Polyethylene Glycol 8000 together at 60° C. and dissolve the salt compound into the melt. Mold this total at 25° C. into appropriate suppositories.

Having described the invention, the embodiments of the invention in which an exclusive property or privilege is claimed are defined as follows:

1. A pharmaceutical composition for inhibiting the growth of leukemic cells comprising in dosage form a cell growth inhibiting amount of 5-cyanopyridine-2-diazohydroxide, alkali metal or alkaline earth metal salt having the formula

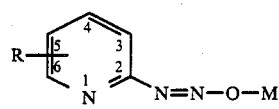

where R is a 5-CN group and M is one equivalent of an alkali metal or one-half equivalent of an alkaline earth metal, and a pharmaceutically acceptable carrier.

2. A pharmaceutical composition according to claim 1 containing 5-cyanopyridine-2-diazohydroxide, sodium salt.

3. A pharmaceutical composition according to claim 1 containing 5-cyanopyridine-2-diazohydroxide, potassium salt.

4. A pharmaceutical composition according to claim 1 containing 5-cyanopyridine-2-diazohydroxide, calcium salt.

5. A pharmaceutical composition according to claim 1 containing 5-cyanopyridine-2-diazohydroxide, magnesium salt.

6. A method for inhibiting the growth of leukemic cells in a mammal which comprises administering a leukemic cell growth inhibiting amount of 5-cyanopyridine-2-diazohydroxide, alkali metal or alkaline earth metal salt having the formula

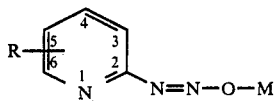

where R is a 5-CN group and M is one equivalent of an alkali metal or one-half equivalent of an alkaline earth metal, in dosage form to a mammal in need thereof.

7. A method according to claim 6 employing 5-cyanopyridine-2-diazohydroxide, sodium salt.

8. A method according to claim 6 employing 5-cyanopyridine-2-diazohydroxide, potassium salt.

9. A method according to claim 6 employing 5-cyanopyridine-2-diazohydroxide, calcium salt.

10. A method according to claim 6 employing 5-cyanopyridine-2-diazohydroxide, magnesium salt.

* * * * *

UNITED STATES PATENT AND TRADEMARK OFFICE
CERTIFICATE OF CORRECTION

PATENT NO. : 4,816,468

DATED : March 28, 1989

INVENTOR(S) : David C. Baker

It is certified that error appears in the above-identified patent and that said Letters Patent is hereby corrected as shown below:

On the face of the patent, "Inventor: David C. Baker, Tuscaloosa, Ala." should be --Inventors: David C. Baker; Elli S. Hand, both of Tuscaloosa, Ala.; Rudiger D. Haugwitz, Bethesda; Venkatachala L. Narayanan, Gaithersburg, both of Md.--.

Signed and Sealed this

Thirteenth Day of March, 1990

*Attest:*

JEFFREY M. SAMUELS

*Attesting Officer*       *Acting Commissioner of Patents and Trademarks*